US00PP35080P2

(12) United States Plant Patent
Werner et al.

(10) Patent No.: US PP35,080 P2
(45) Date of Patent: Apr. 4, 2023

(54) ***CERCIS* PLANT NAMED 'NC2014-10'**

(50) Latin Name: *Cercis canadensis*
Varietal Denomination: NC2014-10

(71) Applicant: North Carolina State University, Raleigh, NC (US)

(72) Inventors: Dennis Werner, Raleigh, NC (US); Leanne M. Kenealy, Durham, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 17/968,127

(22) Filed: Oct. 18, 2022

Related U.S. Application Data

(60) Provisional application No. 63/257,263, filed on Oct. 19, 2021.

(51) Int. Cl.
*A01H 6/00* (2018.01)
*A01H 5/02* (2018.01)

(52) U.S. Cl.
USPC ..... Plt./216

(58) Field of Classification Search
USPC ..... Plt./216
CPC ..... A01H 6/00; A01H 5/02
See application file for complete search history.

(56) References Cited

U.S. PATENT DOCUMENTS

PP17,740 P3 5/2007 Roethling
PP21,451 P3 11/2010 Jackson

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of *Cercis* plant, referred to by its cultivar name 'NC2014-10', is disclosed. The new variety is characterized by its profusion of bright, purple-colored flowers. Plants of the new variety exhibit golden colored, semi-glossy foliage that transitions to green as it ages, and provide moderately vigorous, semi-upright, and semi-compact growth habit.

1 Drawing Sheet

Latin name of genus and species of plant claimed: *Cercis canadensis.*

Variety denomination: 'NC2014-10'.

BACKGROUND OF THE INVENTION

The present invention relates to a new and distinct cultivar of *Cercis* plant botanically known as *Cercis canadensis* and hereinafter referred to by the cultivar name 'NC2014-10'.

The new cultivar originated in a controlled breeding program in Jackson Springs, N.C. in 2006.

The new *Cercis* cultivar is the result of a controlled cross wherein two parents were crossed which previously had been studied in the hope that they would contribute the desired characteristics. The female parent (i.e., the seed parent) of the new cultivar is *Cercis* 'Texas White', not patented. The male parent (i.e., the pollen parent) of the new cultivar is *Cercis* 'Hearts of Gold', U.S. Plant Pat. No. 17,740.

The parentage of the new variety can be summarized as follows:

'Texas White' x 'Hearts of Gold'

The seeds resulting from the above pollination were sown and small plants were obtained which were physically and biologically different from each other. Selective study in 2014 in a controlled environment in Jackson Springs, N.C. resulted in the identification of a single plant of the new variety, which was selected for its profusion of bright, purple-colored flowers, golden colored, semi-glossy foliage that transitions to green as it ages, and moderately vigorous, semi-upright, and semi-compact growth habit.

Asexual reproduction of the new cultivar by chip budding since 2015 in Belvidere, Tenn. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'NC2014-10' as a new and distinct cultivar of *Cercis* plant:

(a) Profusion of bright, purple-colored flowers,
(b) Golden colored, semi-glossy foliage that transitions to green as it ages, and
(c) Moderately vigorous, semi-upright, and semi-compact growth habit.

The new variety of the present invention can readily be distinguished from its ancestors. More specifically, plants of 'Texas White' (i.e., the seed parent) display white-colored flowers, exhibit a rounded habit, and provide dark green and glossy foliage, whereas plants of the new variety display bright, purple-colored flowers, exhibit a semi-uprights and semi-compact growth habit, and provide golden colored and semi-glossy foliage that transitions to green as it ages. In addition, plants of 'Hearts of Gold' (i.e., the pollen parent) display golden colored foliage which emerges as an orange-red color, whereas plants of the new variety display foliage which emerges as golden colored that transitions to green as it ages, and provides larger sized leaves compared to the pollen parent.

Moreover, the new variety can be readily distinguished from other similar non-parental varieties. Of the many commercially available *Cercis* cultivars, the most similar in comparison to the new cultivar is 'JN2', U.S. Plant Pat. No. 21,451. However, plants of the new cultivar differ from plants of 'JN2' in at least the following characteristics:

1. Plants of the new cultivar provides golden colored new growth, whereas the plants of 'JN2' provide golden orange colored new growth, and
2. Plants of the new cultivar have a more compact growth habit than plants of 'JN2'.

BRIEF DESCRIPTION OF THE PHOTOGRAPH

The accompanying photograph shows, as nearly true as it is reasonably possible to make the same in color illustrations of this type the typical growth habit of the new cultivar. Colors in the photographs differ slightly from the color values cited in the detailed description, which accurately describes the colors of 'NC2014-10'. The plant in the photograph was approximately three years old and was growing in a test field in Jackson Springs, N.C.

The drawing illustrates a side view of a tree of 'NC2014-10'

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values of the flowers were determined in spring 2019. Color values of the foliage were determined in summer 2019 under natural light conditions in Jackson Springs, N.C.

The following descriptions and measurements describe plants produced from chip budding and grown outside in Jackson Springs, N.C. Plants were approximately four years of age. Measurements and numerical values represent averages of typical plants.

Botanical classification: *Cercis canadensis* cultivar NC2014-10.

Parentage:

*Female parent.*—*Cercis* 'Texas White', not patented.

*Male parent.*—*Cercis* 'Hearts of Gold', U.S. Plant Pat. No. 17,740.

Propagation:

*Type*.—Chip budding.

Plant description:

*Type*.—Deciduous perennial tree.

*Growth habit and general appearance*.—Moderately vigorous, semi-upright, and semi-compact growth habit.

*Commercial crop time*.—Approximately 1.5 years from budding to finish as a 5 to 6-foot tree.

*Hardiness*.—USDA Zone 6b.

*Size*.—Height of 4-year-old tree: Approximately 7.5 feet. Width: Approximately 5 feet wide.

*Trunk*.—Texture: Rough. Color: Mostly 201A with some spots of N200D.

*Branches*.—Strength: Moderately strong. Diameter of one-year old growth: Approximately 6.0 mm. Stem length of one year old shoots: 22.0 cm. Internode length: 2.0 cm on average. Growth pattern: slightly zigzag, deviating less than 5 degrees from vertical at each node. Texture of new growth: Slightly rugose. Color of young stem: 165A to 200B when hardened off. Lenticel: numerous, tiny. Lenticel length: Less than 1.0 mm. Lenticel shape: circular to slightly elongate. Lenticel color: 164B.

Foliage description:

*General description*.—Type: Deciduous. Arrangement: Alternate.

*Leaves*.—Shape of immature leaves: Suborbicular. Shape of mature leaves: broad-ovate. Apex: Rounded to slightly pointed. Base: Cordate. Margin: Entire. Length to base of sinus: Approximately 8.2 cm. Length to end of lobe: Approximately 11.8 cm. Sinus indentation: Approximately 1.6 cm. Width: Approximately 13.9 cm. Texture of upper and lower surfaces: Smooth, glabrous. Venation pattern: Reticulate. Color of upper surface of immature foliage: N144A to 144A with indistinguishable venation. Color of lower surface of immature foliage: 151B to 144B. Color of upper surface of mature foliage: 143A with indistinguishable venation. Color of lower surface of mature foliage: 138B with indistinguishable venation. Fragrance: None detected.

*Petiole*.—Length: Approximately 3.5 cm. Diameter: Approximately 2.0 mm. Texture: Smooth, glabrous. Color of immature petiole: 35B. Color of mature petiole: 16C.

Flowering description:

*Flowering season*.—Flowers in early spring for about 2-3 weeks depending on weather conditions.

*General description*.—Form: Fasicle. Flower Arrangement: Sessile clusters. Symmetry: Bilateral symmetry. Type: Papilionaceous. Quantity per cluster: 6 per cluster on average. Flower length: 1.3 cm on average. Flower width across wings at anthesis: 8.0 mm on average. Flower depth (bottom of keel petals to top of wings): 1.0 cm on average.

*Bud just before opening*.—Shape: Slightly elongate. Diameter: Approximately 2.0 mm. Length: Approximately 4.0 mm. Color: 167D. Texture: Glabrous.

*Petals*.—Quantity: 5, unfused. Texture of upper and lower surfaces: Glabrous. Color when first and fully open: 72C.

*Calyx*.—Shape: vase-shaped. Diameter: Approximately 6.0 mm at top of hypanthium. Length: Approximately 4.0 mm. Color of outer surface: 560D. Texture of inner and outer surfaces: Glabrous.

*Sepals*.—Arrangement: Fused.

*Pedicel*.—Strength: Strong. Shape: Round. Length: Approximately 7.6 mm. Diameter: Less than 1.0 mm. Texture: Glabrous. Color: 64B.

*Reproductive organs*.—Androecium: Stamen quantity per flower: 10 on average, unfused. Stamen length: 9.0 mm. Stamen width: Less than 1.0 mm. Anther shape: Round. Anther color: 47D. Filament length: 9.0 mm. Filament width: Less than 1.0 mm. Filament color: 62C. Pollen amount: Abundant. Pollen color: 11B. Gynoecium: Pistil length: Approximately 8.0 mm on average. Pistil width: Less than 1.0 mm. Pistil texture: Glabrous. Stigma shape: Round. Stigma color: 62C. Stigma length: Less than 1.0 mm. Stigma width: Less than 1.0 mm. Style shape: Round. Style width: Less than 1.0 mm. Style color: 63B. Ovary position: Superior. Ovary shape: Elongate. Ovary length: 2.0 mm. Ovary width: Less than 1.0 mm. Ovary color: 64C.

*Seed production*.—None observed to date.

*Disease and pest resistance*.—Plants of the new *Cercis* have not been noted to be resistant to pathogens and pests common to *Cercis*.

We claim:

1. A new and distinct cultivar of *Cercis* plant named 'NC2014-10', substantially as herein illustrated and described.

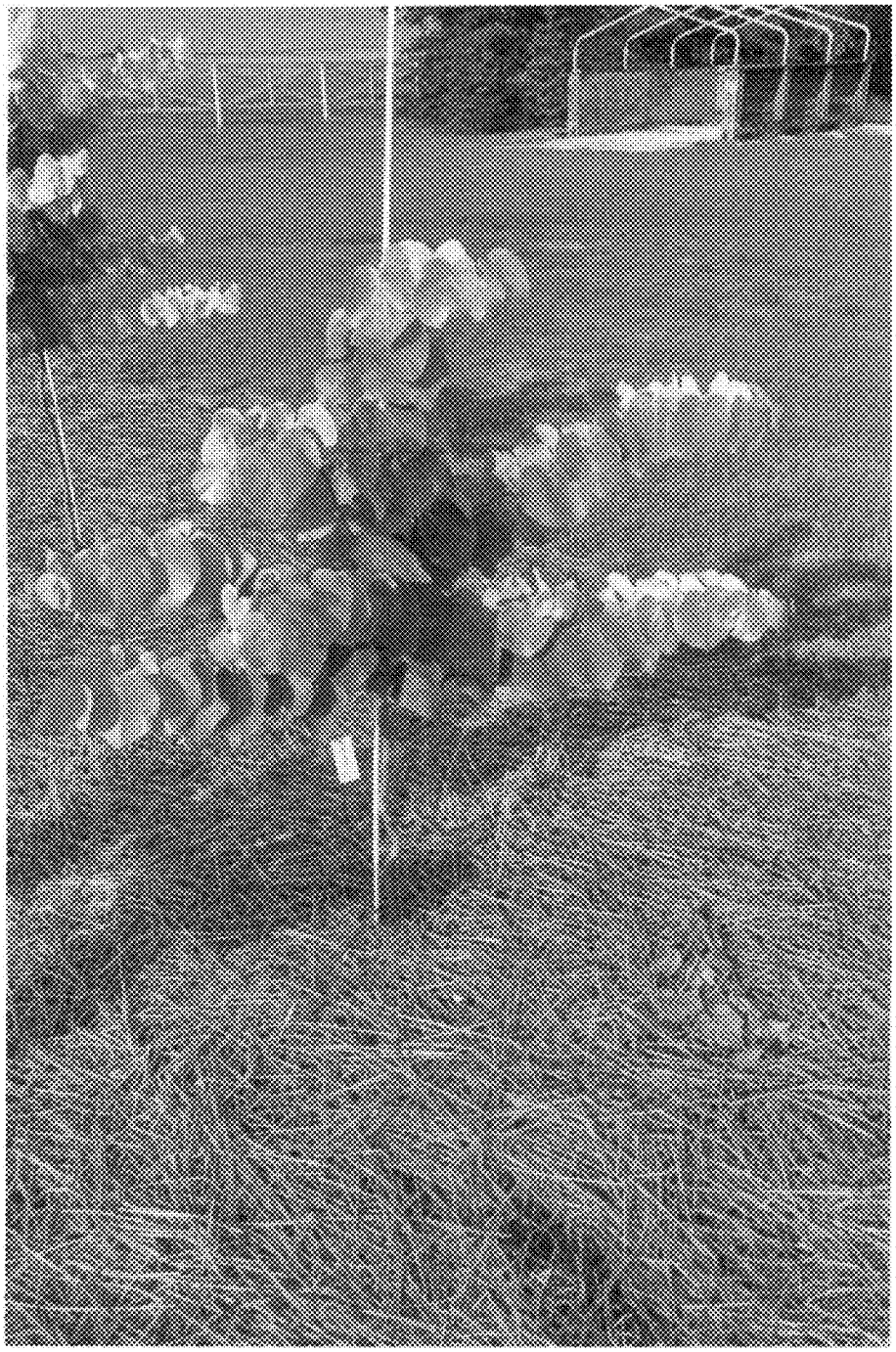

* * * * *